United States Patent [19]

Tsuboshima et al.

[11] Patent Number: 4,512,852

[45] Date of Patent: Apr. 23, 1985

[54] IONIC CONCENTRATION MEASURING APPARATUS AND METHOD

[75] Inventors: Kosaku Tsuboshima, Hachioji; Shigeru Yoshinari, Tokyo, both of Japan

[73] Assignee: Olympus Optical Co., Ltd., Japan

[21] Appl. No.: 587,853

[22] Filed: Mar. 13, 1984

Related U.S. Application Data

[63] Continuation of Ser. No. 433,531, Oct. 8, 1982, abandoned, which is a continuation of Ser. No. 195,641, Oct. 9, 1980, abandoned.

[30] Foreign Application Priority Data

Oct. 18, 1979 [JP] Japan ................................. 54-133574

[51] Int. Cl.³ ............................................ G01N 27/28
[52] U.S. Cl. .................................... 204/1 T; 204/401; 204/402; 204/416; 422/64; 422/67
[58] Field of Search .................. 422/64, 67; 204/1 T, 204/402, 416, 401; 364/497

[56] References Cited

U.S. PATENT DOCUMENTS

| | | | |
|---|---|---|---|
| 3,155,603 | 11/1964 | Hart | 204/402 |
| 3,615,236 | 10/1971 | Tamm | 422/64 |
| 3,684,452 | 8/1972 | Bessman | 422/64 |
| 3,883,306 | 5/1975 | Widen | 422/64 |
| 4,204,917 | 5/1980 | Yamamoto et al. | 422/64 X |

FOREIGN PATENT DOCUMENTS

| | | | |
|---|---|---|---|
| 123695 | 5/1977 | Japan | 204/400 |
| 58592 | 10/1977 | Japan | 204/400 |

*Primary Examiner*—G. L. Kaplan
*Attorney, Agent, or Firm*—Parkhurst & Oliff

[57] ABSTRACT

The disclosed apparatus quickly measures ionic concentration of an electrolyte with an ion sensitive electrode means, by using a number of measuring cups disposed along a circle on a turntable and a series of treating stages fixed along but outside the turntable so as to face different measuring cups as the turntable stops at different angular positions, whereby various treatments necessary for the ionic concentration measurement are carried out simultaneously in parallel at different measuring cups, so as to shorten the measuring time of the ionic concentration.

14 Claims, 5 Drawing Figures

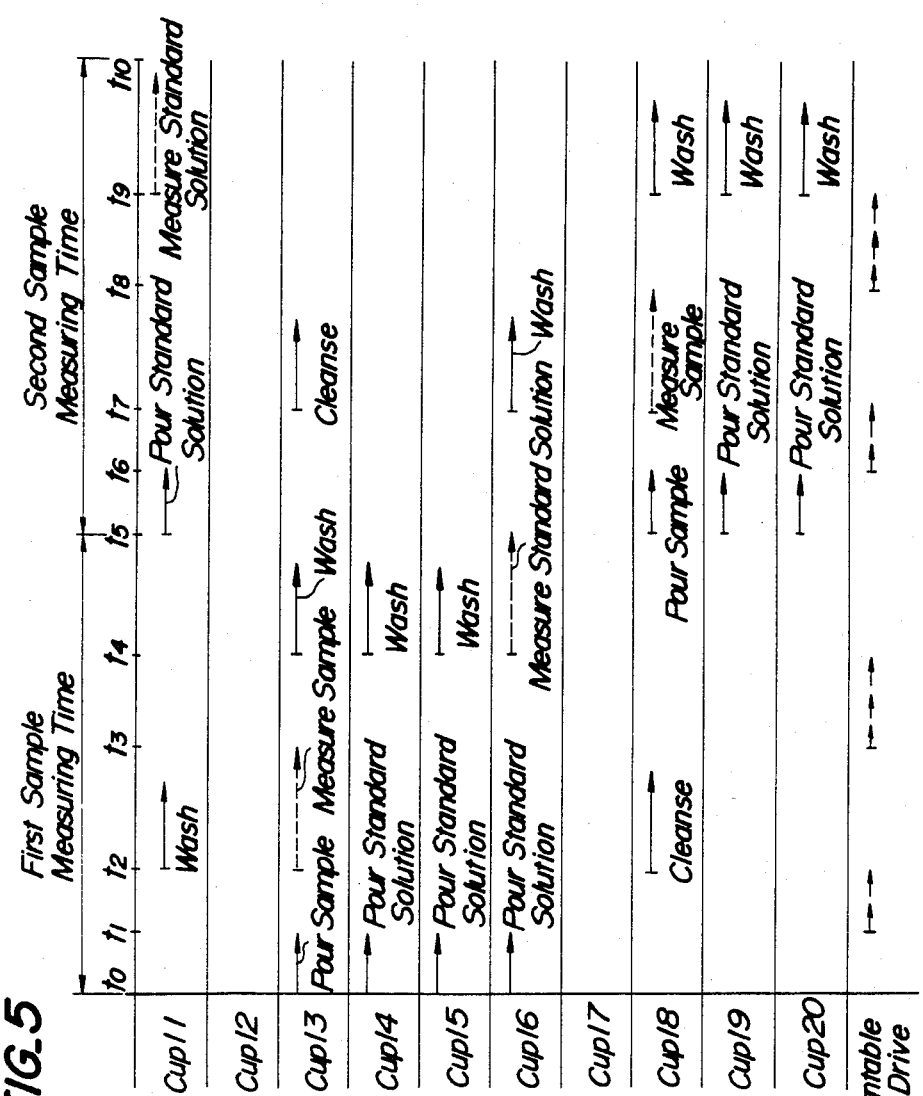

IONIC CONCENTRATION MEASURING APPARATUS AND METHOD

This is a continuation of application Ser. No. 433,531 filed Oct. 8, 1982, which in turn is a Rule 60 Cont. of Ser. No. 195,641, filed Oct. 9, 1980, both now abandoned.

BACKGROUND OF THE INVENTION

1. Field of the Invention

This invention relates to an apparatus for measuring ionic concentration of an electrolyte by using an ion sensitive electrode means.

2. Description of the Prior Art

A typical ionic concentration measuring apparatus of the prior art was disclosed by Japanese Patent Laying-open Specifications No. 58,592/1977 and No. 123,695/1977, which apparatus uses a rotatable sample vessel and a number of treating means disposed right by the sample vessel, such as ion selecting electrodes selectively sensing different ions, a reference electrode, a sample pouring nozzle, a standard solution pouring nozzle, and a draining nozzle. With the aforementioned treating means disposed right by the sample vessel, the apparatus of the prior art carries out a series of operations in succession to measure the ionic concentration; namely, pouring a sample, measuring the ionic concentration of the sample, draining the sample, washing the sample vessel, pouring a standard solution, measuring the standard solution, and draining the standard solution. The measurement of the ionic concentration generally uses ion sensitive electrode means giving a long ion responding time. Accordingly, the ionic concentration measuring apparatus of the prior art has shortcoming in that the measurement of one sample takes a considerably long time.

SUMMARY OF THE INVENTION

Therefore, an object of the present invention is to obviate the aforementioned shortcoming of the prior art, by providing an improved ionic concentration measuring means capable of quick measurement of the ionic concentration.

The inventors noted the fact that the measuring time per sample can be shortened by effecting various treatments on measuring vessels or cups during the period when the measuring electrode means reacts the sample solution, which various treatments include the pouring and draining of the sample, washing of the reaction vessel, the pouring and draining of a standard solution, and the measurement of the standard solution. Thus, the ionic concentration measuring apparatus of the present invention is characterized in that the apparatus comprises a turntable adapted to rotate and stop according to a certain timing schedule, a plurality of measuring cups disposed along a circle on the turntable, and a series of treating means fixed outside said turntable so as to face said measuring cups when said turntable stops, said series of treating means being adapted to simultaneously effect various treatments in parallel for measuring ionic concentration of an electrolyte at different measuring cups, whereby the time necessary for the measurement of the ionic concentration is shortened.

BRIEF DESCRIPTION OF THE DRAWINGS

For a better understanding of the invention, reference is taken to the accompanying drawings, in which:

FIG. 5 is a timing chart describing the operation of the apparatus of FIGS. 3 and 4.

Throughout different views of the drawings, 1 is a sample vessel, 2 is an ion selecting electrode, 3 is a reference electrode, 4 is a sample pouring nozzle, 5 is a standard solution pouring nozzle, 6 is a draining nozzle, 10 is a turntable, 11 through 20 are measuring cups, 21 is a control circuit, 22 is a driving means, 23 is an electrode means, 24 is a sample pouring means, 25 through 27 are standard solution pouring means, 27' is a cleansing means, 28 through 30 are washing means, $P_1$ through $P_9$ are cup stopping angular positions, and 31 is a wiping means.

DETAILED DESCRIPTION OF THE PREFERRED EMBODIMENT

Figure 1:
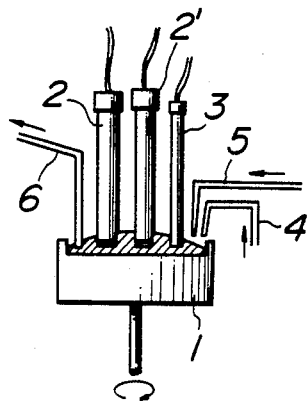
FIG. 1 is a schematic diagram showing the construction of an ionic concentration measuring apparatus of the prior art.
Figure 2:
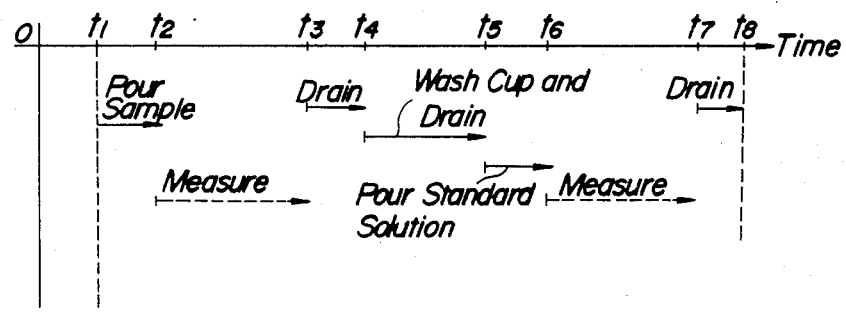
FIG. 2 is a timing chart describing the operation of the apparatus of FIG. 1.

Before entering the details of the invention, an ionic concentration measuring apparatus of the prior art will be briefly reviewed. Referring to FIG. 1, rotatably-supported sample vessel 1 of the prior art receives therein ion selecting electrodes 2, 2', a reference electrode 3, a sample pouring nozzle 4, a standard solution pouring nozzle 5, and a draining nozzle 6. Referring to FIG. 2, the apparatus of FIG. 1 starts its operation by receiving a predetermined amount of a sample solution through the sample pouring nozzle 4 at time $t_1$, measures voltages generated on the ion selecting electrodes 2, 2' in response to the ionic concentrations of the sample solution during the period $t_2$ to $t_3$, and drains the sample solution upon completion of the measurement through the draining nozzle 6 at time $t_3$. At time $t_4$, a standard solution is poured into the sample vessel 1 through the standard solution nozzle 5 to wash the sample vessel 1 and the electrodes 2, 2' and 3, and after the washing the standard solution is drained through the drain nozzle 6. A predetermined amount of the standard solution is fed into the sample vessel 1 through the standard solution nozzle 5 at time $t_5$, so as to measure a voltage generated on the reference electrode 3 in response to the ionic concentration of the standard solution during the period $t_6$ to $t_7$, and finally the standard solution is drained through the draining nozzle 6 at time $t_7$. The ionic concentration of the sample solution is determined by an operational circuit (not shown) based on the difference between the measured voltage relating to the ionic concentration of the sample solution and the measured voltage relating to the ionic concentration of the standard solution.

As pointed out before, the measurement by the apparatus of the prior art is comparatively slow due to the various treatments in series for each sample solution and the comparatively long ion responding time of the ion sensitive electrode.

Figure 3:
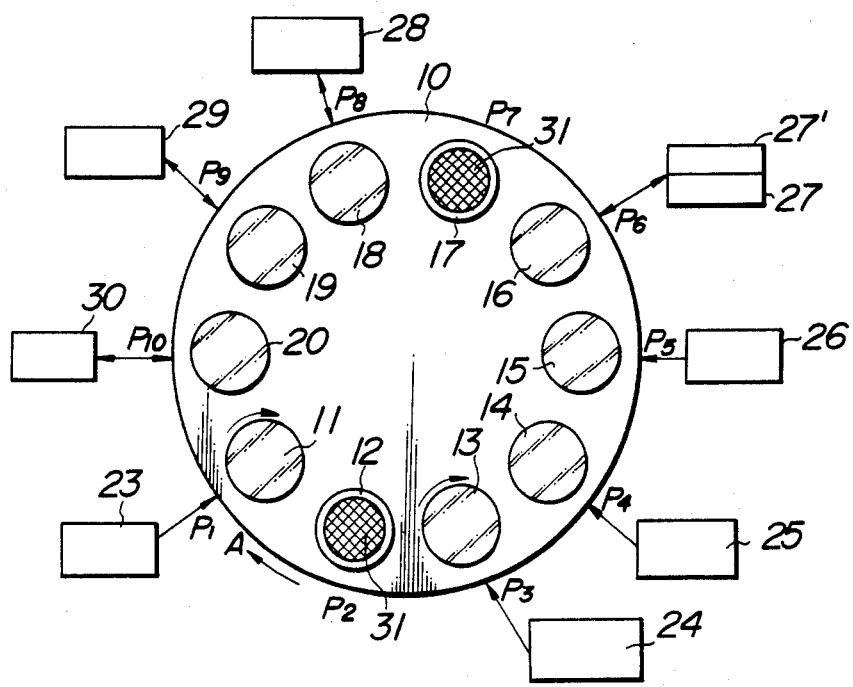
FIG. 3 is a schematic plan view of an ionic concentration measuring apparatus according to the present invention.
Figure 4:
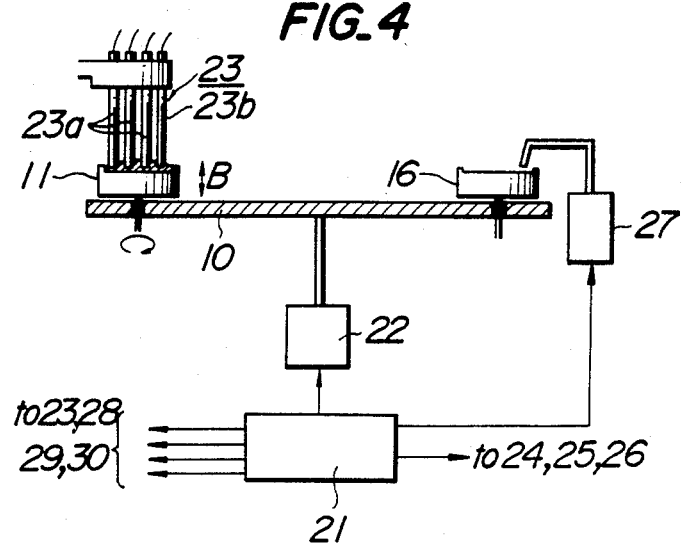
FIG. 4 is a schematic sectional view of the apparatus of FIG. 3.

Referring to FIGS. 3 and 4, the apparatus of the present invention uses a turntable 10 carrying measuring cups 11 through 20 disposed along a circle on the turntable. A control circuit 21 controls a driving means 22 so as to rotate the turntable 10 in steps in the direction of the arrow A with a predetermined timing (see FIG. 5). The measuring cups 11 through 20 stop at angular positions $P_1$ through $P_9$, where various treatments necessary for measuring the ionic concentration are effected. An electrode means including ion selecting electrodes 23a and a reference electrode 23b is disposed at the angular position $P_1$. A sample pouring means 24 is located at the angular position $P_3$. Standard solution pouring means 25, 26, and 27 are located at the positions $P_4$ through $P_6$. The position $P_6$ also carries a cup cleansing means 27'. Cup washing means 28, 29, and 30 are disposed at the positions $P_8$ through $P_{10}$. Various treating means disposed at the positions $P_1$ through $P_{10}$ are controlled by the control circuit 21, so as to operate in a predetermined timing (see FIG. 5). The turntable 10 of the illustrated example also moves vertically at each step of the operation, to allow the electrode means 23 to enter the measuring cup, as shown by the arrow B of FIG. 4. The example of FIGS. 3 and 4 uses ten measuring cups, and five cups are used in turn for one sample solution.

The operation of the ionic concentration measuring apparatus of the invention will now be described by referring to the timing chart of FIG. 5. It is assumed that FIG. 3 shows the conditions at the completion of the measurement of one sample solution. Under the conditions of FIG. 3, the measuring cup 11 carries a standard solution, and the electrodes 23a and 23b are dipped in the standard solution. When a start measurement button (not shown) is actuated at this moment (time $t_0$), a sample solution is poured into the measuring cup 13 at the position $P_3$, and simultaneously, the standard solution is poured into the measuring cups 14, 15, and 16 at the positions $P_4$ through $P_6$ (the measuring cups 14 and 15 are for washing the electrode means 23, while the measuring cup 16 is for measuring the standard solution). During the pouring of the sample solution, the cup 13 is turned about its own axis, to uniformly pour the sample solution in the cup.

At time $t_1$, the turntable 10 is rotated by two steps. In the meantime, as the measuring cup 12 comes to the position $P_1$, a wiping means 31 (for instance, sponge) placed in the cup 12 sweeps the tip surfaces of the electrodes 23a and 23b of FIG. 4. When the measuring cup 13 carrying the sample solution comes to the position $P_1$ (time $t_2$), the electrodes 23a start to measure the electrode voltages for the sample solution. During the measurement of the electrode voltages, the measuring cup 13 is turned about its own axis, to ensure good contact of the electrodes with the sample solution. At the same time, the measuring cup 11 is washed at the position $P_9$, for instance by feeding and draining a suitable washing liquid. The position $P_{10}$ is also for washing, but the measuring cup 12 at the position $P_{10}$ then carries the wiping means 31, so that no washing operation takes place there. The measuring cup 18 at the position $P_6$ is washed at this time.

Upon completion of the measurement of the electrode voltages for the sample solution (moment $t_3$), the turntable 10 is driven by three steps. During those three steps, as the measuring cups 14 and 15 pass the position $P_1$, the standard solution carried by the measuring cups 14 and 15 washes the tip surfaces of the electrodes 23a and 23b, and when the measuring cup 16 comes to the position $P_1$ (moment $t_4$), the reference electrode 23b measures the electrode voltage of the standard solution in the measuring cup 16. During this measurement, the measuring cup 16 is rotated about its own axis. At the same time, the measuring cups 13, 14, and 15 are washed at the positions $P_8$, $P_9$, and $P_{10}$. When the measurement of the electrode voltage for the standard solution is completed at the moment $t_5$, an operational circuit (not shown) determines the ionic concentration of the sample solution based on the electrode voltages for the sample solution and the electrode voltage for the standard solution, and the ionic concentration thus determined is displayed. Thus, the measurement for one or a first sample solution is finished.

The measurement of the next following or a second sample solution is effected by the measuring cups 11 and 17 through 20 during the period $t_5$ to $t_{10}$ of FIG. 5 in a similar manner. More particularly, at the moment $t_5$, the sample solution is poured into the measuring cup 18 at the position $P_3$, while the standard solution is poured into the measuring cups 19, 20, and 11 at the positions $P_4$ through $P_6$. At the moment $t_6$, the turntable 10 is driven by two steps. When the turntable 10 is thus driven, the wiping means 31 or sponge in the measuring cup 17 wipes the tip surfaces of the electrodes at the position $P_1$. When the measuring cup 18 comes to the position $P_1$, the sample solution therein is measured. During this measurement ($t_7$ to $t_8$), the measuring cup 16 is washed at the position $P_9$, while the measuring cup 13 used in the preceding measurement is cleansed at the position $P_6$. At the moment $t_8$, the turntable 10 is driven by three steps, during which three steps, the electrode tip surfaces at the position $P_1$ are washed by the standard solution carried by the measuring cups 19 and 20 and the measurement of the standard solution is carried out when the measuring cup 11 is at the position $P_1$. During this measurement ($t_9$–$t_{10}$), the measuring cups 18, 19, and 20 are washed at the positions $P_8$, $P_9$, and $P_{10}$. Whereby, the measurement of this sample is completed.

As described in the foregoing, in the ionic concentration measuring apparatus according to the present invention, various treatments necessary for measuring the ionic concentration of the sample solution are carried out in parallel by assigning such treatments to different measuring cups, so that the measuring time is greatly shortened as compared with that of the prior art as shown in FIGS. 1 and 2. The measuring time of the apparatus of the invention is reduced substantially to the electrode reaction time. Although the construction of the prior art apparatus is complicated because of the congestion the electrodes and various means for feeding and draining sample and standard solutions at the location of the sample vessel as shown in FIG. 1, the construction of the apparatus of the invention is simple because various means are distributed around the turntable. It is noted that the sample cups 13 and 18 must be thoroughly washed and cleansed, and in the illustrated example of the invention, the sample cups 13 and 18 are used alternately during the measurements of the first and second sample solutions and washed and cleansed twice at the positions $P_8$ and $P_6$, so as to prevent the measuring cups 13 and 18 from contamination by all means. Furthermore, at the end of each measurement, the cup 11 or 16 carrying the standard solution therein comes to the position $P_1$, so that the electrodes are protected by the standard solution against and deterioration of their service lives.

The present invention is not restricted to the illustrated embodiment, but numerous changes and modifications thereof are possible. For instance, although the turntable of the illustrated example carries measuring cups for two sample solutions, it is possible to dispose many more measuring cups on the turntable for dealing with three or more sample solutions to effect the ionic concentration measurement in a similar manner. Moreover, the number of the measuring cups per one sample solution can be made less than or more than five.

What is claimed is:

1. A method of measuring an ionic concentration of samples, comprising:
   pouring a sample into a sample receiving cup;
   pouring washing liquid into at least one washing liquid receiving cup;
   pouring standard solution into a standard solution receiving cup, each of said cups being disposed on a rotatable turntable;
   measuring the ion concentration of the sample solution in said sample receiving cup with an ion measuring electrode means;
   washing said ion measuring electrode means in said washing liquid receiving cups;
   measuring the ion concentration of the standard solution in said standard solution receiving cup with said ion measuring electrode means;
   wiping said ion measuring electrode means by bringing said ion measuring electrode means into contact with a liquid absorbing member contained in an electrode receiving cup carried by said turntable; and
   discharging the sample solution, the washing liquid and the standard solution from the sample receiving cup, the washing liquid receiving cup and the standard solution cup, respectively, after these cups have passed through the ion measuring electrode means.

2. A method as claimed in claim 1, wherein said ion measuring electrode means is washed by standard solution between successive measurements of successive samples.

3. A method as claimed in claim 2, wherein said washing liquid is said standard solution.

4. A method as claimed in claim 1, wherein the steps of pouring sample and pouring standard occur simultaneously.

5. A method as claimed in claim 1, further comprising washing one of said cups with a cup washing means.

6. A method as claimed in claim 5, wherein said washing one of said cups occurs simultaneously with the measurement of the ion concentration of said sample solution.

7. An apparatus for measuring ionic concentration of successive samples comprising a turntable adapted to rotate and stop at a predetermined timing, a plurality of measuring cups disposed about a circle on the turntable, ion sensitive electrode means provided at a measuring position and a control means for inserting and removing the electrode means into and out of the measuring cups in synchronization with the intermittent movement of the turntable, wherein the improvement comprises:
   a sample pouring means for delivering successive samples into measuring cups, the sample pouring means located at a sample pouring position;
   an electrode washing liquid pouring means for delivering an electrode washing liquid into measuring cups, the electrode washing liquid pouring means being located at a washing liquid pouring position;
   electrode wiping means comprising a liquid absorbing member contained in an electrode receiving cup carried by the turntable;
   a standard solution pouring means for delivering a standard solution having a known ion concentration into measuring cups, the standard solution pouring means being located at a standard solution pouring position; and
   a measuring cup washing means for washing the measuring cups, the measuring cup washing means being located at a measuring cup washing means position which corresponds to a position upon the turntable;
   wherein the control means for inserting and removing the electrode means into and out of the measuring cups in synchronization with the intermittent movement of the turntable is constructed to provide for the ion sensitive electrode means to be exclusively inserted into the measuring cups into which the samples, the electrode washing liquid and the standard solution have been delivered, with all of said means operating at substantially the same instant.

8. The apparatus of claim 7, wherein the electrode washing liquid comprises the standard solution.

9. The apparatus of claim 7, including means for stopping the turntable only when the measuring cups containing the samples and the standard solution arrive at the measuring position.

10. The apparatus of claim 7, wherein the electrode washing liquid pouring means comprises two delivery devices arranged successively adjacent the periphery of the turntable.

11. The apparatus of claim 7, wherein the measuring cup washing means comprises three washing devices arranged successively adjacent the periphery of the turntable.

12. The apparatus of claim 7, wherein the measuring position, the sample pouring position, the electrode washing liquid pouring position, the standard solution pouring position and the measuring cup washing positions are located around the circumference of the turntable in the aforementioned order when viewing the turntable in a direction which is opposite to the rotating direction of the turntable.

13. The apparatus of claim 12, wherein the turntable carries ten measuring cups; when the first measuring cup is positioned at the measuring position, the third cup is in the sample pouring position, the fourth and fifth cups are in the electrode washing position, the sixth cup is in the standard solution pouring position, the eighth, ninth and tenth cups are in the washing position, and the second and seventh cups contain sponge members for wiping the standard solution from the electrode means.

14. The apparatus of claim 13, including means for rotating the turntable in alternating increments corresponding to moving two steps and three steps, respectively.

* * * * *